United States Patent [19]

Greb et al.

[11] Patent Number: 4,537,771

[45] Date of Patent: Aug. 27, 1985

[54] ANTACIDS CONTAINING ZEOLITIC MOLECULAR SIEVES

[75] Inventors: Wolfgang Greb; Peter Christophliemk; Christine Schröder, all of Duesseldorf, Fed. Rep. of Germany

[73] Assignee: Henkel Kommanditgesellschaft auf Aktien, Duesseldorf, Fed. Rep. of Germany

[21] Appl. No.: 514,140

[22] Filed: Jul. 15, 1983

[30] Foreign Application Priority Data

Jul. 30, 1982 [DE] Fed. Rep. of Germany ....... 3228485

[51] Int. Cl.³ .............................................. A61K 33/06
[52] U.S. Cl. ..................................... 424/154; 424/155; 424/157
[58] Field of Search ......................... 424/154, 155, 157

[56] References Cited

U.S. PATENT DOCUMENTS 4,379,143  4/1983  Sherry et al. ........................ 424/154

FOREIGN PATENT DOCUMENTS 103429   1/1974   German Democratic Rep. .
53-20437 2/1978   Japan ................................... 424/154
1257594 12/1971   United Kingdom .

OTHER PUBLICATIONS

Chemical Abstracts—99: 43570X, European Patent Office, Search Report.

Primary Examiner—Frederick E. Waddell
Attorney, Agent, or Firm—Ernest G. Szoke; Henry E. Millson, Jr.; Mark A. Greenfield

[57] ABSTRACT

Antacids containing zeolitic sodium aluminosilicates and/or potassium aluminosilicates of the A, X, Y, or P type molecular sieves with pharmaceutical adjuvant material. Such antacids are useful in the treatment of gastric hyperacidity and other related conditions.

23 Claims, 4 Drawing Figures

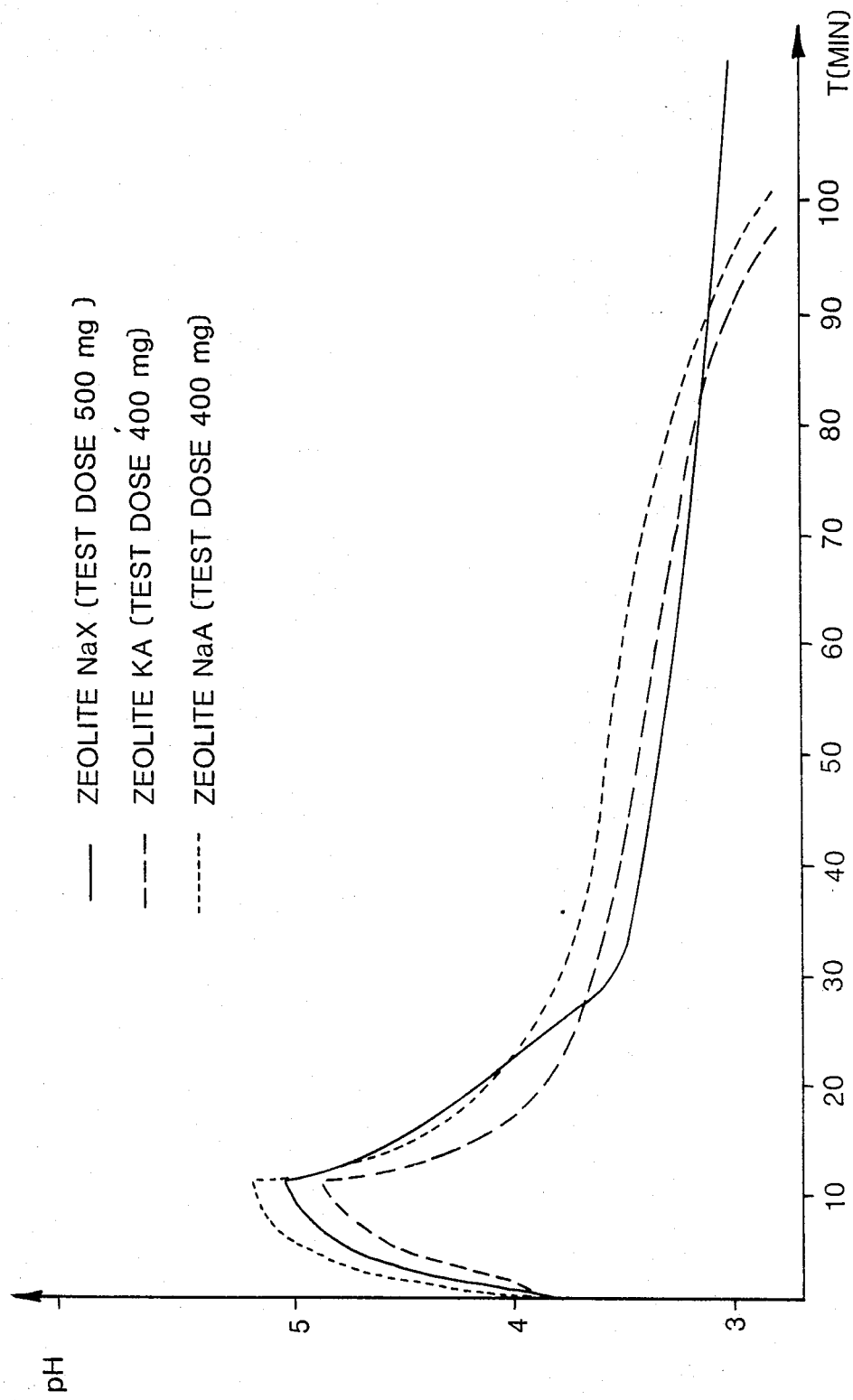

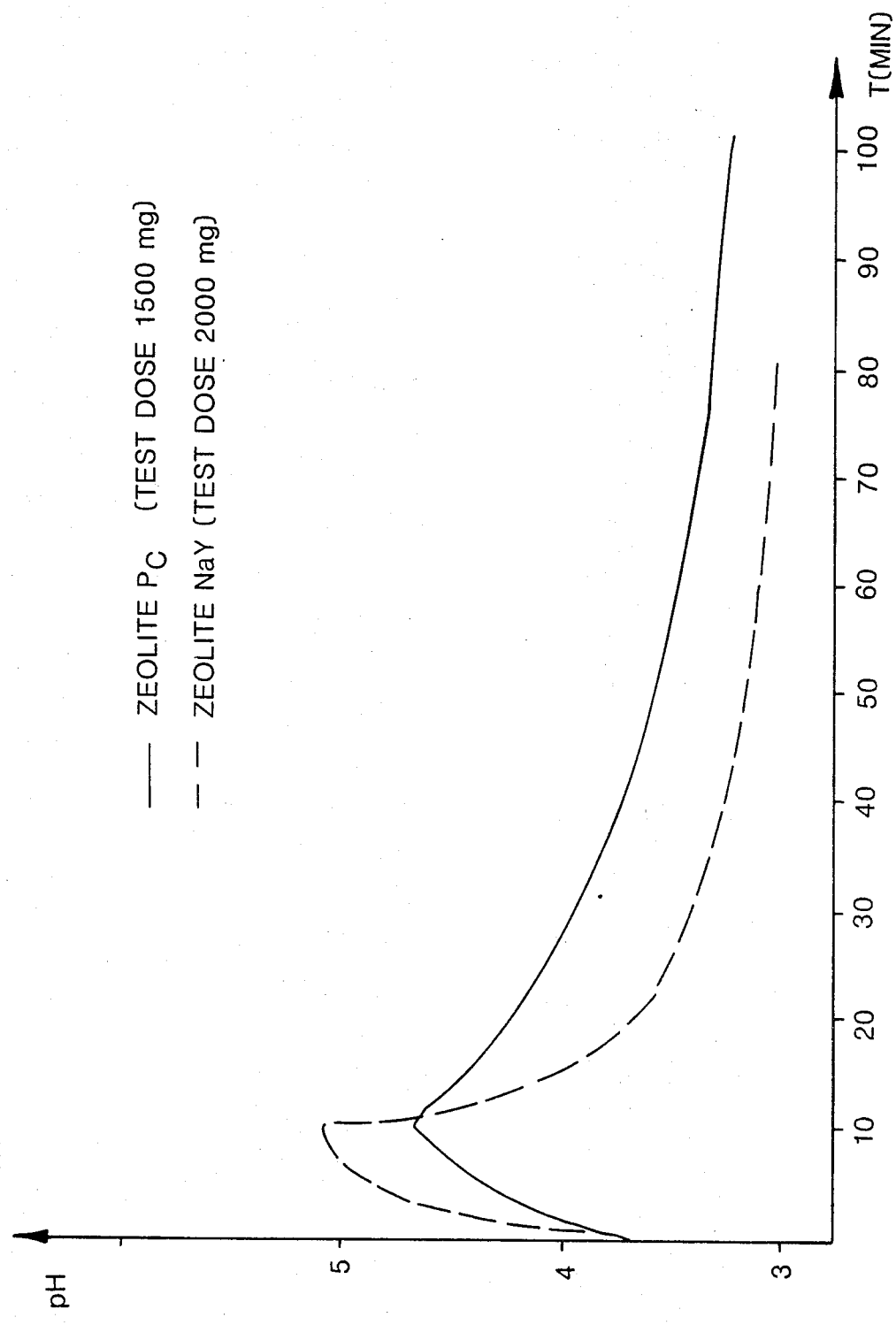

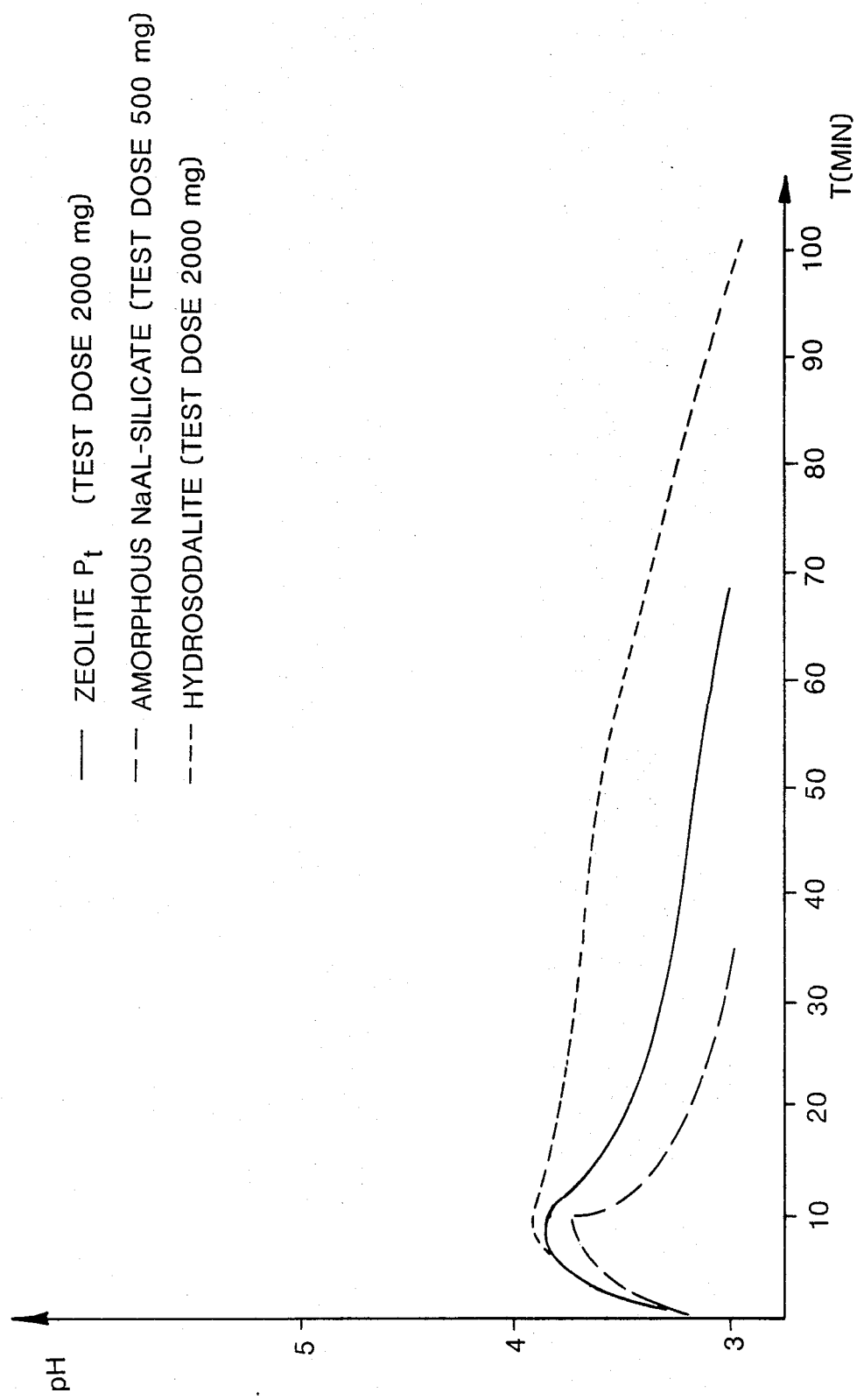

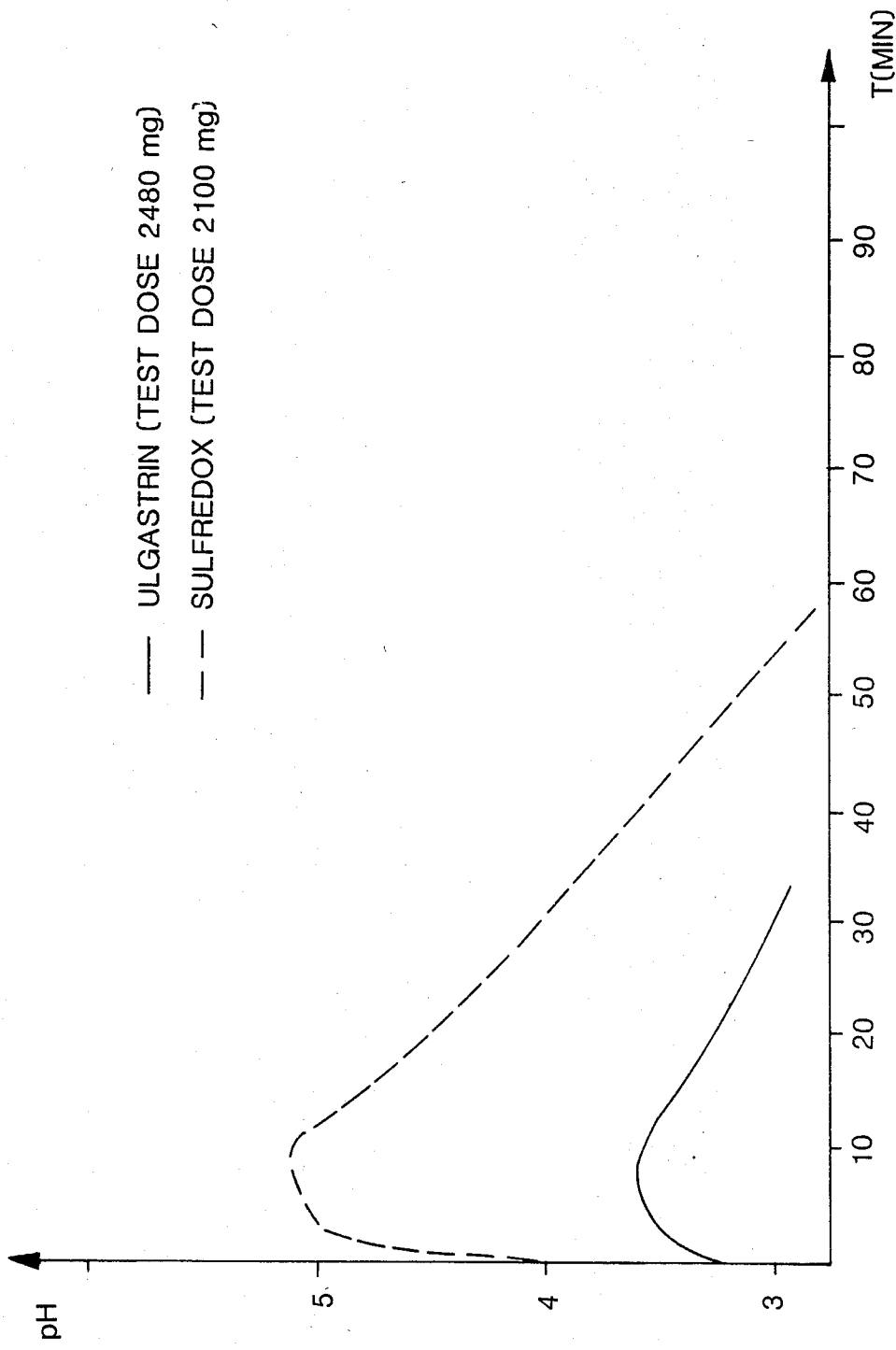

ANTACIDS CONTAINING ZEOLITIC MOLECULAR SIEVES

BACKGROUND OF THE INVENTION

This invention relates to antacids containing zeolitic alkali aluminosilicates of A, X, Y, or P type molecular sieves or mixtures thereof in their sodium and/or potassium forms. The invention also relates to the use of zeolitic alkali aluminosilicates of A, X, Y, or P type molecular sieves or mixtures thereof in their sodium and/or potassium forms for the production of antacids and the use thereof in the treatment of hyperacidity and related conditions.

Antacids are medicaments which neutralize excess stomach acid. They are indicated for stomach disorders caused by hyperacidity and for hyperacidity-related Ulcus ventriculi or Ulcus duodemi. Further indications include heartburn acidic eructation, feeling of fullness, hyperacidity, reflux oesophagitis, heartburn in pregnancy, stomach complaints after alcohol and nicotine abuse and after errors in diet, hiatus hernia, colitis, treatment and prophylaxis of the "stress ulcer", Gastrophatia neurogenica, medication-related hyperacidity and also "upset" stomach.

Accordingly, antacids are not only particularly important in the treatment of ulcers, they are also the most widely prescribed medicaments, even though in most instances they can be obtained without a prescription. The state of the art in this field is exemplified by the following publications: W. Leetsch, Deutsche Apothekerzeituny 114, 1307 (1974) "Antacida und das Problem ihrer Wirksamkeitsbeurteilung (Antacids and the Problems of Assessing their Effectiveness)"; H. Ruppin, Med. Klin. 70, 1237 (1975) "Theoretische und Klinische Aspekte der Antacidatherapie" (Theoretical and Clinical Aspects of Antacid Therapy) ; K. H. Holtermüller, E. Bohlen, M. Castro and H. J. Weis, Med. Klin. 72, 1229 (1977) "Uberlegungen zur Therapie mit Antacida (Reflections on Therapy with Antacids)"; H. Brunner, E. Penner and G. Grabner, Öst. Arztetg. 32/1, 27 (1977) "Sind Antacida Plazebos? (Are Antacids Placebos?)"; R. Gllüer, Schweiz. med. Wschr. 107, 807 (1977) "Pufferkapazität und Kosten der flüssigen Antazida 1977 (Buffer Capacity and Costs of Liquid Antacids 1977)"; S. B. Siskin, University of Michigan, Medical Center Journal 40, 93 (1974) "Over the Counter Drug Review: Antacid Products"; J. Schnekenburger, Arzneim.-Forsch. (Drug Res.) 24, 142 and 275 (1974) "In-vitro-Untersuchungen an Antazida (in vitro Studies of Antacids)"; J. Schnekenburger, Loc.cit. 31 (II), 1286 (1981) "In-vitro-Untersuchungen an Antacida (In-vitro Studies of Antacids)".

This prior art contains information on the chemical action of antacids, lists advantages and disadvantages of market preparations and describes galenic forms thereof, evaluation criteria, cost/profit ratios and methods for the in-vitro testing of antacids.

The most common substances active as antacids are sodium bicarbonate, calcium carbonate, magnesium carbonate, aluminum hydroxide, aluminum phosphate, magnesium trisilicate, aluminum magnesium trisilicate hydrate, and sodium aluminum silicate. Most, if not all, of these active substances have undesirable side effects which are of importance, particularly when the substances in question are taken regularly. Sodium bicarbonate reacts very quickly with the stomach acid to form carbon dioxide (troublesome gas production); excess sodium bicarbonate is absorbed (particularly troublesome in the case of hypertonics) and displaces the acid-base equilibrium to the alkaline side (causing alkalosis, milk alkali syndrome). Alkaline reaction in the stomach brought about by excess sodium bicarbonate gives rise to compensatory acid production, commonly referred to as "acid rebound".

These effects also occur when calcium carbonate is taken. In addition, during the actual neutralization phase, calcium carbonate produces an increase in the release of gastrin which in turn stimulates the secretion of acid. Considerable quantities of calcium are absorbed, and especially in the event of repeated application, can lead to renal calcinosis.

Magnesium salts have a laxative effect. Also, due to the danger of accumulation, they are contraindicated in cases of renal malfunction.

When taken over a prolonged period (2 to 3 weeks), aluminum salts formed as reaction products of aluminum-containing antacids cause phosphate depletion. In addition, emptying of the stomach is delayed by inhibition of the contraction of the smooth musculature and slight blockage can occur.

Silicates used as antacids produce the same side effects as magnesium and aluminum salts. In general, however, treatment with these antacids is regarded as safe. The antacid silicates bind acid while leaving a certain residual acidity.

German Patent Application DE No. 20 29 265 describes an antacid mixture which contains sodium aluminum silicate and milk powder. However, this sodium aluminum silicate is not a zeolitic sodium aluminosilicate, as can be seen from the following discussion.

Although the term "sodium aluminum silicate" is a generic term for all products of the type $xNa_2O \cdot Y \, Al_2O_3 \cdot z \, SiO_2$ for x, y, Z$\neq$0, the term does exclude compounds of the type in which the aluminum is attached to the silicate tetrahedrons in the form of an $AlO_4$ tetrahedron, i.e. through oxygen bridges. This is apparent from standard text books on inorganic chemistry, for example those by Remy 12th Edition, Vol. I, page 615, 1965) or Holleman-Wiberg (81st – 90th Edition, pages 553-554, 1976) in which the latter, tetrahedron-attached compounds are distinctly referred to as "sodium aluminosilicates". Gmelin (XI*, XII*) Volume "Aluminum Part B" also distinguishes between "sodium aluminum silicates" and "zeolites".

Accordingly, German Patent Application DE No. 20 29 265 excludes zeolitic antacids. This is also confirmed by the following statement in the descriptive part of this Application (page 3/4): "Irrespective of the route selected for oral ingestion, aluminum sodium silicate has an extremely disagreeable taste and is very unpleasant to take". A "disagreeable" taste is a well known characteristic of sodium aluminum silicates of the type defined above containing $Al^{3+}$-cations which are not tetrahedrally surrounded by oxygen. Zeolitic sodium alumosilicates on the other hand have a neutral taste which cannot be characterized as "disagreeable".

East German Pat. No. 103,429 describes a process for the production of a sodium alumosilicate gel which corresponds to the composition $Na_2O \cdot Al_2O_3 \cdot 2SiO_2 \cdot$ aq and which has antacid properties. On page 2, left-hand column, this East German Patent describes highly crystalline molecular sieves (zeolites) as prior art and states that, although these zeolites show certain acid-binding properties, these antacid properties are not sufficient to enable the zeolites in question to be pharmaceutically used as antacids. Accordingly, compounds other than zeolites, namely sodium aluminum silicate gels, are produced in East German Pat. No. 103,429 where they are said to be suitable for use as antacids. This prior art teaches those skilled in the art not to use zeolitic, and hence crystalline, sodium aluminum silicates as antacids. During the development of the present invention tests were conducted for comparison with the teachings of the East German Pat. No. 103,429 and are discussed in detail hereinafter.

DESCRIPTION OF THE INVENTION

The object of the present invention is to provide antacids which, while showing favorable buffer properties, do not have any of the above-mentioned disadvantages of conventional antacids, including in particular the release of physiologically harmful ions. The improved antacids of the invention are useful in the treatment of hyperacidity and similar symptoms.

In particular, the present invention relates to antacids which contain zeolitic sodium aluminosilicates and/or potassium aluminosilicates of the A, X, Y or P type molecular sieves and mixtures thereof together with standard pharmaceutically acceptable antacid excipients.

The present invention also relates to the use of zeolitic sodium aluminosilicates and/or potassium aluminosilicates of the A, X, Y or P type molecular sieves or mixtures thereof for the production of antacids and in the use of such antacids in the treatment of hyperacidity and related symptoms.

Zeolites having a high cation-exchange capacity are preferred for use herein. This cation exchange capacity can be defined as the "calcium binding power" (Ca BP) and is determined as follows:

The calcium binding power of 1 g of sodium aluminosilicate (active substance=AS) per liter for an initial hardness of 30° d H (deutsche Harte=German Hardness) is used as a measure of the cation exchange capacity of zeolites. To determine calcium binding power, 1 liter of an aqueous solution containing 0.594 g of $CaCl_2$ (corresponding to 300 mg of CaO/1 =30° d H) is adjusted with dilute sodium hydroxide solution to a pH-value of 10, followed by the addition of 1 g of AS. The suspension formed is then vigorously stirred for 15 minutes at a temperature of 22 ±2° C. After the solid has been filtered off, the residual hardness X in the filtrate is determined by complexometric titration using ethylene diamine, tetraacetic acid. The calcium binding power in mg of CaO/g of AS is calculated from the result obtained in accordance with the formula (30−X)·10.

The zeolitic alkali metal aluminosilicates used in the practice of the invention have a calcium binding power (CaBP) of more than 70 mg and preferably at least 100 mg of CaO/g of aluminosilicate (active substance).

Preferred zeolites include the A, X, Y and P type molecular sieves of the NaA, NaX, NaY, $NaP_c$, KA, KX, KY and $KP_c$ types and also mixtures thereof. The chemical compositions of NaA and KA type molecular sieves correspond to the following formulae:

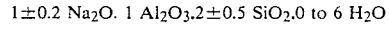

and

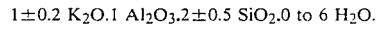

Those of the NaX and KX type molecular sieves, which are richer in silicate, have the following formulae:

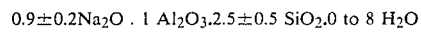

and

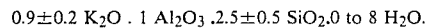

Those of the NaY and KY type molecular sieves, which are even richer in silicate, have the following formulae:

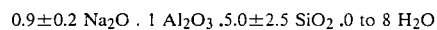

and

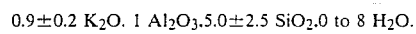

These three types show considerable similarity in the structure of their aluminosilicate lattice.

The chemical composition of the P type molecular sieve, which is also referred to as "zeolite $P_c$" or "molecular sieve B", corresponds to the following formulae (for the $NaP_c$ and $KP_c$ types):

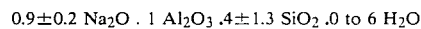

and

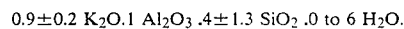

The X-ray diffractogram of the molecular sieve NaA is shown for example in German Applications DE No. 10 38 015 and No. 10 38 017; that of the molecular sieve NaX in German Application DE No. 10 38 016; and that of the molecular sieve NaY in German Pat. No. 1,203,239.

The X-ray diffractogram of $NaP_c$ is shown for example in D. W. Breck's book entitled "Zeolite Molecular Sieves", New York 1974, page 365.

Using an in-vitro titration method described by Schnekenburger loc.cit., which is discussed in the Examples, buffer times of 60 to 90 minutes were observed with the zeolites used in accordance with the invention in quantities of from about 300 to about 2000 mg. By contrast, distinctly poorer buffer results were obtained with various amorphous alkali metal aluminosilicates, zeolite $P_t$ (tetragonal form), hydrosodalite and similar, structurally related aluminosilicates. In these tests, various NaMg-silicates having a lamina structure and also sodium silicates (metasilicates, kanemite, magadiite) also performed poorly for the most part. Only hectorite showed sufficiently good buffer behavior for use as an antacid, although its chemical composition (NaMg-silicate containing lithium fluoride) prevents it from being used as an antacid on medical grounds (cf. side effects of Mg salts).

The in-vitro method used also showed that, in addition to the Na-forms of the zeolites used in accordance with the invention, their K-forms are also usable as antacids without any loss of effect. The latter discovery can also be utilized to medicinal advantage because, by partial use of the K-types, not only is it possible to obtain a physiologically safe concentration of absorbable Na ions in the gastro-intestinal tract, it is even possible to adjust physiologically the most favorable $Na^+/K^+$ ion ratio. Numerical data which can be used to determine favorable mixing ratios of sodium and potassium types for the zeolitic antacids used in accordance with the invention can be found in the work by W. Siegenthaler entitled "Klinische Pathophysiologie", Keyword "Wasser- und Elektrolythaushalt", Thieme 1976, pages 197–201.

The X-ray amorphous sodium aluminosilicates described in the Examples of East German Patent No. 103,429 and produced accordingly showed unfavorable buffer results in the in-vitro titration test.

According to their respective manufacturers, the commercially available preparations "ULGASTRIN ®" and SULFREDOX ®" contain "sodium aluminum silicate". In order to be able to identify this component, samples of these two antacids were titrated and treated with hot water. The dried residue was examined by X-ray photography. Zeolitic structures could not be detected in either product. The presence of the A, X, Y or $P_c$ zeolites, used in accordance with the present invention, in these commercial preparations can definitely be ruled out. Also, in-vitro titration tests produced good buffering results only with "SULFREDOX".

The zeolitic alkali metal aluminosilicates employed in accordance with the invention to form antacid compositions for oral ingestion are formulated with pharmaceutical adjuvant materials commonly used with antacid compositions. The zeolitic alkali metal aluminosilicate can be used alone or can be used in combination with other active ingredients such as milk powders and milk fractions; antiflatulent agents such as dimethylpolysiloxane (simethicone); plant extracts such as carrageenan, alginic acid, etc.; magnesium carbonate; calcium carbonate; magnesium bicarbonate; calcium bicarbonate; sodium bicarbonate; aluminum hydroxide; magnesium hydroxide; aluminum phosphate; magnesium trisilicate; aluminum magnesium trisilicate hydrate; sodium aluminum silicate; and the like. Obviously, however, since the present zeolitic alkali metal aluminosilicates do not produce the deletereous side effects of some of these other active ingredients, it is preferable to either use them as the sole active ingredient or use them in combination with other active ingredients that do not produce such side effects, e.g. simethicone, plant extracts, etc. The present compositions can be formulated into coated or pressed tablets; capsules; dragées; liquid suspensions; powders or granules; effervescent compositions in powdered, granular or tablet form; sustained release formulations with known sustained release excepients and dosage forms; and the like. Unit dosage forms thereof conveniently contain from about 200 mg. to about 1000 mg, preferably from about 300 to about 600 mg, of zeolitic alkali metal aluminosilicates. When such aluminosilicates are formulated with other active ingredients, the quantity of aluminosilicate present can be reduced proportionally; however, the quantity of aluminosilicate present should generally not be less than about 100 mg per unit dose, and the total quantity of active ingredients is usually within the above ranges.

The above formulations are generally administered to a patient, normally a human patient, suffering from a condition for which antacid treatment is indicated at a dosage level of from about 2 to about 30 mg, preferably about 4 to about 18 mg of zeolitic alkali metal aluminosilicate per kg body weight. This dosage level can be administered from once a day to up to six times a day, preferably 3 or 4 times a day. Obviously, when combinations with other active ingredients are used, the above dosage levels are adjusted to take into account the effects of the other active ingredients.

The following examples are intended to illustrate the invention and not to limit it.

EXAMPLES

Using Schnekenburger's method (loc.cit. 31 (II), 1286 (1981)), the quantity of the antacid to be tested was added at 37° C. to a medium of synthetic gastric juice and water and The change in the pH-value of the resulting suspension as a function of time was recorded. 10 minutes after the antacid had been added, more synthetic gastric juice was added and, after another 10 minutes, the volume added to the reaction mixture (i.e. suspension equal in volume to the synthetic gastric juice added) was removed. This removal was repeated at intervals of 10 minutes until the pH-value fell to below 3. Dosage and removal were automatically controlled.

The synthetic stomach acid (acid concentration 0.084 mole/liter) had been freshly prepared by dissolving 0.32 g of pepsin RN and 0.2 g of sodium chloride R and adding 2.8 ml of 3N hydrochloric acid to a total of 100 ml in accordance with DAB 8 (page 74, Keyword "Pepsin-Losung (pepsin solution)").

The instruments used included an Autoburette ABU 12, a Dosimat Metrohm E 415, a Haake FY recirculation thermostat, a CG 811 pH-meter with an N 61 glass electrode, a Servopor Z 10 recorder, and a thermostatically controlled measuring vessel equipped with a magnetic stirrer.

For automatic titration, 20.0 ml of synthetic gastric juice and 20.0 ml of distilled water were introduced into the measuring vessel. After the measuring temperature of 37° C. had been reached, the dose of antacid to be tested (in this case by definition 1/5th of the individual dose) was introduced into the measuring vessel with stirring and, at the same time, the recorder was switched on. After 10 minutes, the introduction of synthetic gastric juice was started and, after another 10 minutes, the automatic removal of 5.0 ml of reaction mixture was commenced.

A buffering time of 60 to 90 minutes was the desired goal of the test. To this end, the antacids were used in corresponding dosages. Differences between the buffering capabilities are shown up in this way.

The aluminosilicates used for the titration tests in the Examples are described in the following Table I in regard to their chemical composition, their production and their origin.

TABLE I

| Chemical composition of the alkali aluminosilicates tested for antacid activity | | | | | | |
|---|---|---|---|---|---|---|
| | Chemical composition based on $Al_2O_3 = 1.0^a$ | | | | | |
| Name | $Na_2O$ | $K_2O$ | $SiO_2$ | % $H_2O^b$ | Ca $BP^c$ | Remarks |
| Zeolite NaA | 1.0 | — | 2.0 | 20.0 | 170 | Type HAB A 40, a product of Degussa |
| Zeolite KA | 0.1 | 0.9 | 2.0 | 15.0 | 135 | HAB A 40 exchanged with $K^{+d}$ |
| Zeolite NaX | 1.0 | — | 2.5 | 12.5 | 120 | Type 13 X, a product of UCC |
| Zeolite NaY | 1.0 | — | 3.1 | 24.3 | 100 | Laboratory product |

TABLE I-continued

Chemical composition of the alkali aluminosilicates tested for antacid activity

| Name | Chemical composition based on $Al_2O_3 = 1.0$[a] | | | % $H_2O$[b] | Ca BP[c] | Remarks |
|---|---|---|---|---|---|---|
| | $Na_2O$ | $K_2O$ | $SiO_2$ | | | |
| Zeolite $P_c$ | 1.0 | — | 3.3 | 12.0 | 130 | " |
| Zeolite $P_t$ | 1.1 | — | 3.7 | 15.5 | 10 | " |
| Hydrosodalite | 1.1 | — | 2.0 | 9.1 | 5 | " |
| Amorphous NaAl silicate | 0.7 | — | 2.0 | 16.1 | 140 | Produced in accordance with East German Patent No. 103,429/ Example 1 |
| | 0.4 | — | 2.1 | 19.5 | 7 | Produced in accordance with East German Patent No. 103,429/ Example 2 |

[a] as determined by X-ray fluorescence analysis
[b] ignition loss after 30 minutes/800° C.
[c] cf. determination procedure on page 6
[d] treated three times with dilute KCl solution; product contains approximately 90% of KA and 10% of NaA.

The titration curves of the Examples are shown in FIGS. 1 to 4 below. FIGS. 1 and 2 show the titration curves of the zeolites used in accordance with the invention while FIGS. 3 and 4 show the titration curves of the compositions of the prior art.

EXAMPLES 1 and 2 of East German Pat. No. 103,429 were copied and the products obtained titrated in the manner described; the test dose of 500 mg producing the titration curve shown in FIG. 3 (amorphous NaAl silicate) which indicates poor buffering behavior. It was not possible even by altering the dosage (test dose 300 –2000 mg) to obtain a significantly different curve or even a more favorable curve (with respect to the desired maximum at approx. pH 5).

The titration curves of the commercial products ULGASTRIN and SULFREDOX are shown in FIG. 4, from which it can be seen that only SULFREDOX approaches a useful curve which, however, nonetheless produces a much shorter buffering time than the zeolites used in accordance with the invention.

It is apparent from Schnekenburger's Articles (loc.-cit.), that, with the planned dosage and the corresponding test dose, the maximum value of the titration curves after 10 minutes should tie at pH 5. The pH-value of approximately 3.0 which corresponds to the normal acidity of the stomach should be reached after at most 60 minutes, a slower reduction in the pH-value corresponding to a longer buffering time naturally being preferred.

What is claimed is:

1. An antacid composition comprising
(a) an antacid effective quantity of at least one zeolitic alkali metal aluminosilicate, having a calcium binding power (Ca BP) of at least about 100 mg of CaO/g of aluminosilicates, of the A, X, Y, or P type molecular sieve, wherein the alkali metal is sodium or potassium or both sodium and potassium; and
(b) antacid adjuvant materials.

2. An antacid composition in accordance with claim 1 wherein at least one zeolitic alkali metal aluminosilicate is of the A type having the following formula:

$$1 \pm 0.2\ Z_2O\ .\ 1\ Al_2O_3\ .2 \pm 0.5\ SiO_2\ .0\ to\ 6\ H_2O$$

wherein Z is Na, K, or both Na and K.

3. An antacid composition in accordance with claim 1 wherein at least one zeolitic alkali metal aluminosilicate is of the X type having the following formula:

$$0.9 \pm 0.2 Z_2O\ .\ 1\ Al_2O_3\ .2.5 \pm 0.5\ SiO_2\ .0\ to\ 8\ H_2O$$

wherein Z is Na, K, or both Na and K.

4. An antacid composition in accordance with claim 1 wherein at least one zeolitic alkali metal aluminosilicate is of the Y type having the following formula:

$$0.9 \pm 0.2\ Z_2O\ .\ 1\ Al_2O_3\ .5.0 \pm 2.5\ SiO_2\ .0\ to\ 8\ H_2O$$

wherein Z is Na, K, or both Na and K.

5. An antacid composition in accordance with claim 1 wherein at least one zeolitic alkali metal aluminosilicate is of the $P_c$ type having the following formula:

$$0.9 \pm 0.2\ Z_2O\ .\ 1\ Al_2O_3\ .4 \pm 1.3\ SiO_2\ .0\ to\ 6\ H_2O$$

wherein Z is Na, K, or both Na and K.

6. An antacid composition in accordance with claim 1 wherein said composition also contains at least one other antacid effective material.

7. An antacid composition in accordance with claim 1 in unit dosage form for oral ingestion wherein the unit dosage form contains an antacid effective quantity of zeolitic alkali metal aluminosilicate.

8. An antacid composition in accordance with claim 7 wherein the unit dosage form contains from about 200 to about 1000 mg of zeolitic alkali metal aluminosilicate.

9. An antacid composition in accordance with claim 8 wherein from about 300 to about 600 mg of zeolitic alkali metal aluminosilicate is present therein.

10. An antacid composition in accordance with claim 6 in unit dosage form for oral ingestion wherein the unit dosage form contains an antacid effective quantity of antacid effective materials.

11. An antacid composition in accordance with claim 10 wherein the unit dosage form contains a total of from about 200 to about 1000 mg of antacid effective materials.

12. An antacid composition in accordance with claim 11 wherein from about 300 to about 600 mg of antacid effective materials are present therein.

13. An antacid composition in accordance with claim 1 wherein said composition is in liquid suspension form.

14. An antacid composition in accordance with claim 1 wherein said composition is in powdered or granular form.

15. An antacid composition in accordance with claim 14 wherein said composition effervesces in contact with water.

16. A method for treating a physiological condition in a mammalian body that is benefited from treatment with an antacid comprising administering to said mammalian body an antacid effective quantity of the antacid composition of claim 1.

17. A method in accordance with claim 16 wherein the physiological condition is or is accompanied by hyperacidity.

18. A method in accordance with claim 16 wherein the mammalian body is a human body.

19. A method in accordance with claim 18 wherein the antacid composition is administered orally.

20. A method in accordance with claim 19 wherein from about 2 to about 30 mg of zeolitic alkali metal aluminosilicate per kilogram body weight is administered.

21. A method in accordance with claim 20 wherein said quantity is administered from 1 to 6 times per day.

22. A method in accordance with claim 18 wherein the antacid composition of claim 6 is administered.

23. A method in accordance with claim 16 wherein the mammalian body is a human body, the antacid composition is administered orally, and the antacid composition of claim 8 is administered in amount sufficient to provide from about 4 to about 18 mg of antacid active materials per kilogram of body weight.

* * * * *